United States Patent [19]

Satomura

[11] Patent Number: 4,707,553
[45] Date of Patent: Nov. 17, 1987

[54] INDOLE DERIVATIVES AND PROCESS FOR PRODUCING THE SAME

[75] Inventor: Masato Satomura, Kanagawa, Japan

[73] Assignee: Fuji Photo Film Co., Ltd., Kanagawa, Japan

[21] Appl. No.: 687,328

[22] Filed: Dec. 28, 1984

[30] Foreign Application Priority Data

Dec. 28, 1983 [JP] Japan .................................. 58-248910

[51] Int. Cl.$^4$ .................... C07D 401/12; C07D 209/08
[52] U.S. Cl. ..................................... 546/273; 548/159; 548/440; 548/455; 548/460; 548/462; 548/463; 548/483
[58] Field of Search ............... 548/483, 489, 440, 455, 548/159, 460, 462, 463; 546/273

[56] References Cited

PUBLICATIONS

H. Wasserman et al., Tetrahedron Letters, No. 7, pp. 33–36 (1960).
R. Sundberg, The Chemistry of Indoles, p. 397 (1970), Academic Press, N.Y.
R. Morrison et al., Organic Chemistry, Allyn and Bacon, Inc. (1973), Boston, p. 772.
W. C. Sumpter et al., The Chemistry of Heterocyclic Compounds, vol. 8, Interscience Pub. (1954).
Yuki Goesikagaku Kyokaushi, 38 694 (1980) (English abstract attached thereto).
J. Am. Chem. Soc., 88, 2536 (1966), G. Allen et al., The Mitomycin Antibiotics, Synthetic Studies XIV, The Nenitzescu Indole Synthesis.

*Primary Examiner*—Mary E. Ceperley
*Attorney, Agent, or Firm*—Sughrue, Mion, Zinn, Macpeak and Seas

[57] ABSTRACT

A 5-hydroxy-N-substituted indole derivative and the process for producing the indole derivative are described the indole derivative is produced by a process comprising reacting a phenol derivative having an unsaturated double bond in the m-position with a diazonium salt.

2 Claims, No Drawings

INDOLE DERIVATIVES AND PROCESS FOR PRODUCING THE SAME

FIELD OF THE INVENTION

The present invention relates to a process for producing indole derivatives and, particularly, 5-hydroxyindole derivatives.

BACKGROUND OF THE INVENTION

Indole derivatives having a hydroxyl group in the 5-position are important compounds as starting materials for a series of antibiotics known as mitomycin type compounds. A number of processes for synthesizing indole derivative are known, such as Fischer's process, Bischler's process, Nenitzescu's process, Reissert's process, Hinsberg's process, Madelung's process, Stolle's process or Brunner's process. In Fischer's process, the general method comprises using hydrazine as a starting material, forming hydrazone and reacting with acid with heating. However, it is impossible to simply obtain indoles having a hydroxyl group in the 5-position (see Ishii: Yuki goseikagaku kyokaishi, 38 694 (1980)) using such a process.

In Bischler's process, α-anilinoketone is used as a starting material and allowed to react with acid at a high temperature to carry out a dehydration reaction. However, since the reaction condition is severe, it is difficult to obtain 5-hydroxyindoles.

Nenitzescu's process comprises reacting a benzoquinone derivatives with enamine. According to this process, although indoles having a hydroxyl group the in the 5-position are formed, the yield thereof is poor. In addition, there is a disadvantage in that the process is restricted to production of, chiefly, compounds wherein an electron attractive group such as an acyl group or an alkoxycarbonyl group, etc. is introduced into the 3-position of the indole ring, because reagents wherein an electron attractive group attaches to the double bond of enamine are generally used in order to stabilize enamine (see Allen; J. Am. Chem. Soc., 88,2536 (1966)).

General Processes for forming an indole ring have been disclosed in detail in Sumpter: "Heterocyclic Compounds with Indole and Carbazole Systems" 1954, Interscience, New York, but 5-hydroxy derivatives are not described.

Further, as another process, it has been attempted to synthesize, for example, 5-hydroxy-3-methylindole by oxidizing an indole ring precursor such as dihydroskatole with potassium nitrosodisulfonate. However, this process has disadvantage in that the operation is troublesome and the yield is poor.

SUMMARY OF THE INVENTION

An object of the present invention is to provide a process for producing indole derivatives, wherein the indole derivatives are obtained in a good yield under a mild condition by a simple operation.

The object of the present invention has been met by a process for producing 5-hydroxy-indole derivatives comprising reacting a phenol derivative having an unsaturated double bond in the m-position with a diazonium salt.

DETAILED DESCRIPTION OF THE INVENTION

The process of the present invention is represented by the following reaction scheme.

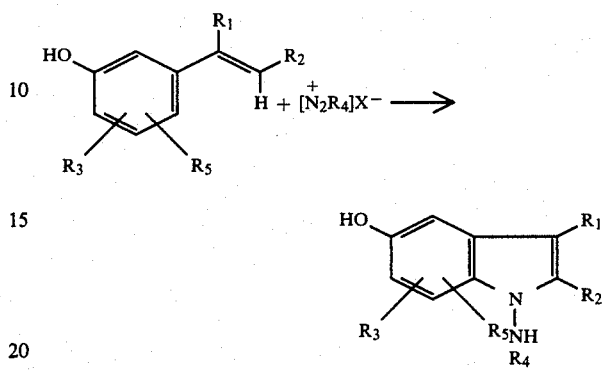

wherein $R_1$, $R_2$ are each selected from the group consisting of a hydrogen atom, an alkyl group having 1 to 8 carbon atoms, an aralkyl group having 7 to 10 carbon atoms, an aryl group having 6 to 8 carbon atoms and an alkoxy group having 1 to 3 carbon atoms, and $R_3$ and $R_5$ are each selected from the group consisting of a hydrogen atom, an alkyl group having 2 to 6 carbon atoms, a halogen atom, an alkenyl group having 2 to 6 carbon atoms, an acyl group having 2 to 4 carbon atoms, an aryl group having 6 to 8 carbon atoms, an aralkyl group having 7 to 10 carbon atoms, and an alkoxy group having 1 to 5 carbon atoms and the p-position to the hydroxyl group of the phenol derivative having an unsaturated double bond may have a hydrogen atom or a group which is released by a diazo-coupling reaction such as a halogen atom, etc. $R_4$ represents a residue of a diazonium salt. $N_2{}^+R_4$ represents a diazonium ion produced from a diazonium salt and $X^-$ is an anion, i.e., an ion pair of the diazonium ion and represents an organic or inorganic monovalent anion, such as $Cl^-$, $ZnCl_3{}^-$, $BF_4{}^-$, $HSO_3{}^-$, $PF_6{}^-$, $NO_3{}^-$, $CH_3C_6H_4SO_3{}^-$, etc.

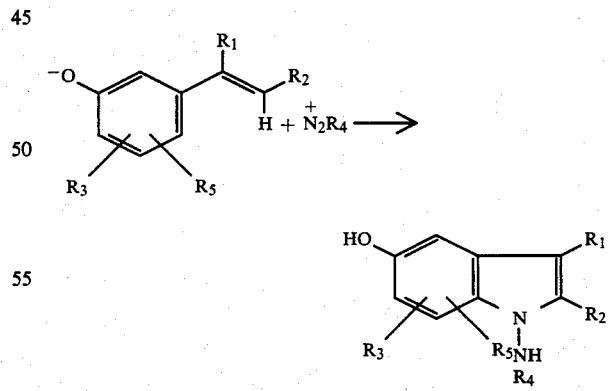

The previously described reaction substantially proceeds in the above described manner.

A hydrogen atom and an alkyl group having 1 to 3 carbon atoms are most preferable for $R_1$ and $R_2$, a hydrogen atom, a halogen atom such as a chlorine atom and a bromine atom, an alkyl group having 1 to 5 carbon atoms and an alkoxy group having 1 to 5 carbon atoms are most preferable for $R_3$ and $R_5$.

As be understood from the reaction formula, the reaction of the present invention has an advantage that a high yield is attained under a mild condition, because it does not include a step of forming water, alcohol or amine, etc., which is different from the prior processes. In the present invention, the exact kind of intermediate that is formed during formaton of the indole ring is not completely known, but it is believed that, after diazocoupling is carried out once on the p-position to the hydroxyl group, the keto form of quinonimine is formed and proton transfer being about formation of an indole ring.

In the process of the present invention, as the phenol derivatives having an unsaturated double bond in the m-position, there are phenol derivatives having a carbon-carbon unsaturated double bond in the m-postion wherein the β-position of the unsaturated bond has at least one hydrogen atom, such as 3-vinylphenol, 3-isopropenylphenol, 3-isopropenyl-6-chlorophenol, 3-isopropenyl-6-bromophenol, 3allylphenol, 3-α-phenylvinylphenol, 3-α,β-dimethylvinylphenol, 2-methoxy-5-vinylphenol, 3-isopropenyl-6-methylphenol, 3-α,β-dimethylvinyl-6-methylphenol, 3-isopropenyl-6-ethylphenol, 3-cyclohexenyl-phenol, 3-isopropenyl-5-methylphenol, 3-isopropenyl-5,6-dimethylphenol 2-methoxy-5-isopropenylphenol and 3,5-diisopropenylphenol, etc.

On the other hand, as components for carrying out a diazo-coupling reaction, compounds which form a conventional diazonium salt are advantageously used, and aromatic amines are preferably utilized. The aromatic ring may be any of a benzene ring and naphthalene ring which are composed of carbon atoms, or may be a ring having one or more hetero atoms such as a nitrogen atom, an oxygen atom or a sulfur atom, etc., such as a pyridine ring, a thiazole ring or a furan ring. Further, it may be a condensed ring such as a benzothiazole ring or benzofuran ring.

Further, these aromatic rings may have one or more of alkoxy groups, alkyl groups, carboxyl group, sulfo group, dialkylamino groups, nitro group, alkoxycarbonyl groups, halogen atoms, thioalkoxy groups and hydroxyl group, etc.

Aromatic amines having at least one amino group capable of forming a diazonium salt, for example, aniline, anisidine, chloroanisidine, chloroaniline, phenetidine, dichloroaniline, toluidine, chlorotoluidine, nitroaniline, aminobenzoic acid, aminobenzene-sulfonic acid, aminonaphtholsulfonic acid, aminonaphthol-disulfonic acid, α-aminonaphthalene, diaminobenzene, aminobenzothiazole, aminocoumarin, aminocarbazole, aminomethylnaphthylidin-2-ol, N-4-amino-2-methylphenyl-4-chlorophthalimide, Variamine Blue B, aminobenzene, amino-methoxybenzothiazole, aminomethoxypyridine and aminomethyl-benzothiazole, aminosalycilic acid, etc. are advantageously used.

The diazo reaction is carried out under a conventional condition, for example, as described in Zollinger; "Azo and diazo chemistry", 1961, Interscience, New York. The diazo reaction is preferably carried out at a temperature of about 30° C. to about −15° C. using a solvent such as a water; an organic solvent, e.g., an alcohol, a nitrile, a ketone, an ether, an amide, a sufone, a halide, an aryl solvent, etc.; and a mixture thereof. As a solvent, more specifically, a methanol, an ethanol, an isopropanol, an acetone, an acetonitrile, a dimethylformamide, a dimethylsulfoxide, a dichloroethane, a chloroform, a toluene, a xylene, water-toluene mixture, water-dichloroethane mixture, etc. are used. A used amount of the solvent is preferably about 100 ml or less per 0.002 mole of diazotized compound in view of an easiness of post-treatment of the reaction.

The substituent on the 1-position of indole obtained as described above is subjected quantitatively to a releasing reaction by a catalytic reduction.

The process of the present invention is illustrated in detail with reference of the following nonlimiting examples.

EXAMPLE 1

600 ml of methanol and 0.2 mols of m-isopropenylphenol were placed in a 3-necked flask equipped with a stirrer and a thermometer, and 0.28 mols of potassium hydroxide and 30 ml of water were added with passing a nitrogen gas. The mixture was then stirred while reducing the temperature to 10° C. or less. To the mixture, a diazonium salt formed from 0.22 mols of aniline and 0.23 mols of sodium nitrite was added over 15 minutes, and the mixture was stirred at 5° C. for 1 hour. It was then neutralized with 5 wt% of ice-cooled hydrochloric acid to form a precipitate.

The precipitate was washed with water and recystallized from benzene to obtain reddish orange crystals having a melting point of 144°–5° C. and a molecular weight of 238. Yield 80%. NMR analysis comfirmed that the produced was 1-anilino-3-methyl-5-oxyindole.

When the resulting product was subjected to a catalytic reduction with Raney nickel using methanol as a solvent at 70° C. under a hydrogen pressure of 70 kg/cm$^2$, aniline and 3-methyl-5-oxyindole (which was recrystallized from benzene, melting point 110°–110.5° C.) were quantitatively obtained.

Thus, it was confirmed that the skeleton of the above described product was an anilino form.

Further, the above described product was reacted with an equivalent amount of acetic anhydride in tetrahydrofuran, subsequently added into water to form a precipitation and filtered followed by drying. The acetylated product thus obtained has 1 mol of acetyl group. Melting point: 163°–4° C. Molecular weight: 280. When the above described product was processed with potassium hydroxide-dimethyl sulfate according to the conventional process, a monomethyl derivative having a melting point: 84°–5° C. and molecular weight: 252 was obtained.

EXAMPLE 2

The same procedure as in Example 1 was carried out, but anthranilic acid was used as the aromatic amine and 0.56 mols of alkali were used. After carring out a diazocoupling reaction, an aqueous solution of potassium hydroxide was added to completely dissolve the product. Then, it was neutralized with 10 wt% of hydrochloric acid to precipitate crystals. The crystals were washed with water to obtain red crystals. Yield: 85%

According to mass spectral analysis, the molecular weight was 282, and a strong peak of the molecular weight: 146 caused by release of the 2-carboxyanilino group was observed. By comparing this spectrum with that of the spectrum of the compound in Example 1, this compound was confirmed as 1-(2-carboxy-anilino)-3-methyl-5-oxyindole.

While the invention has been described in detail and with reference to specfic embodiments thereof, it will be apparent to one skilled in the art that various changes and modifications can be made therein without departing from the spirit and the scope thereof.

What is claimed is:

1. A process for poducing 5-hydroxy-N-substituted indoles having the following formula (I) comprising reacting a phenol derivative having the following general formula (II) with a diazonium salt having the following general formula (III)

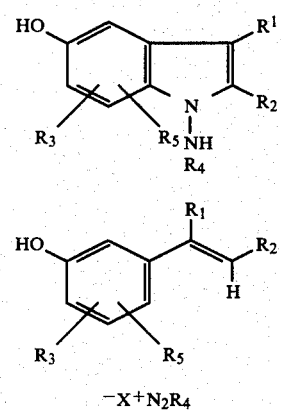

$$-X^+N_2R_4 \quad \text{(III)}$$

wherein $R_1$, $R_2$ are each selected from the group consisting of a hydrogen atom, an alkyl group, an aralkyl group, an aryl group and an alkoxy group, and $R_3$ and $R_5$ are each selected from the group consisting of a hydrogen atom, an alkyl group, a halogen atom, an alkenyl group, an acyl group having 2 to 4 carbon atoms, an aryl group, an aralkyl group and an alkoxy group, $R_4$ represents a diazonium salt residue which is a substituted or unsubstituted aromatic amine selected from the group consisting of aniline, anisidine, chloroanisidine, chloroaniline, phenetidine, dichloroaniline, toluidine, chlorotolunidine, nitroaniline, aminobenzoic acid, aminobenzenesulfonic acid, aminonaphtholsulfonic acid, aminonaphtholdisulfonic acid, α-aminonaphthalene, diaminobenzene, aminobenzothiazole, aminocoumarin, aminocarbazole, amino-methylnaphthylidin-2-ol, N-4-amino-2-methylphenyl-4-chlorophthalimide, N-(p-methoxyphenyl)-p-phenylenediamine (Variamine Blue B), amino-methoxybenzothiazole, aminomethoxypyridine, aminomethyl-benzothiazole, and aminosalycilic acid and $-X$ is an anion.

2. A process of claim 1, wherein the diazonium salt is prepared by a diazotization of an aromatic amine selected from the group consisting of aniline, anisidine, chloroanisidine, chloroaniline, phenetidine, dichloroaniline, toluidine, chlorotoluidine, nitroaniline, aminobenzoic acid, aminobenzene-sulfonic acid, aminonaphtholsulfonic acid, aminonaphthol-disulfonic acid, α-aminonaphthalene, diaminobenzene, aminobenzothiazole, aminocoumarin, aminocarbazole, aminomethylnaphthylidin-2-ol, N-4-amino-2-methylphenyl-4-chlorophthalimide, N-(p-methoxyphenyl)-p-phenylenediamine (Variamine Blue B), aminobenzene, amino-methoxybenzothiazole, aminomethoxypyridine aminomethyl-benzothiazole, and aminosalycilic acid.

* * * * *